US010557160B2

(12) United States Patent
Ellington et al.

(10) Patent No.: US 10,557,160 B2
(45) Date of Patent: Feb. 11, 2020

(54) TRANSGENIC BACTERIA WITH EXPANDED AMINO ACID USAGE AND NUCLEIC ACID MOLECULES FOR USE IN THE SAME

(71) Applicant: BOARD OF REGENTS, THE UNIVERSITY OF TEXAS SYSTEM, Austin, TX (US)

(72) Inventors: Andrew D. Ellington, Austin, TX (US); Ross Thyer, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 58 days.

(21) Appl. No.: 15/380,560

(22) Filed: Dec. 15, 2016

(65) Prior Publication Data

US 2017/0166945 A1 Jun. 15, 2017

Related U.S. Application Data

(60) Provisional application No. 62/267,498, filed on Dec. 15, 2015.

(51) Int. Cl.
| | |
|---|---|
| *C12P 21/06* | (2006.01) |
| *C12P 21/02* | (2006.01) |
| *C12N 9/86* | (2006.01) |
| *C12N 9/00* | (2006.01) |
| *C12N 15/11* | (2006.01) |

(52) U.S. Cl.
CPC ............ *C12P 21/02* (2013.01); *C12N 9/86* (2013.01); *C12N 9/93* (2013.01); *C12N 15/11* (2013.01); *C12Y 305/02006* (2013.01)

(58) Field of Classification Search
None
See application file for complete search history.

(56) References Cited

U.S. PATENT DOCUMENTS

| 9,464,288 B2 | 10/2016 | Soll et al. | |
|---|---|---|---|
| 2014/0154744 A1* | 6/2014 | Soll | C07K 14/47 435/69.6 |
| 2014/0303084 A1 | 10/2014 | Thorn et al. | |
| 2015/0050682 A1 | 2/2015 | Hondal et al. | |
| 2017/0166945 A1 | 6/2017 | Ellington | |

FOREIGN PATENT DOCUMENTS

| WO | WO 01/12657 | 2/2001 | |
|---|---|---|---|
| WO | WO-2013009868 A1 * | 1/2013 | ............. C07K 14/47 |

OTHER PUBLICATIONS

Score report result for SEQ ID No. 18 for Soll et al U.S. Appl. No. 14,131,382 (Year: 2014).*
Score result for WO-2013009868-A1 (above) (Year: 2013).*
Aldag, Caroline, et al. "Rewiring Translation for Elongation Factor Tu-Dependent Selenocysteine Incorporation." *Angewandte Chemie International Edition* 52.5 (2013): 1441-1445.
International Search Report and Written Opinion issued in International Application No. PCT/US2017/041373, dated Nov. 17, 2017.
Invitation to Pay Additional Fees issued in International Application No. PCT/US17/49354, dated Nov. 17, 2017.
Miller, Corwin, et al. "A synthetic tRNA for EF-Tu mediated selenocysteine incorporation in vivo and in vitro." *FEBS letters* 589. 17 (2015): 2194-2199.
Mueller, Sabine, et al. "The formation of diselenide bridges in proteins by incorporation of selenocysteine residues: biosynthesis and characterization of (Se) 2-thioredoxin." *Biochemistry* 33.11 (1994): 3404-3412.
Safavi-Hemami, Helena, et al. "Specialized insulin is used for chemical warfare by fish-hunting cone snails." *Proceedings of the National Academy of Sciences* 112.6 (2015): 1743-1748.
Thyer, Ross, et al. "Evolving tRNASec for efficient canonical incorporation of selenocysteine." *Journal of the American Chemical Society* 137.1 (2014): 46-49.

* cited by examiner

*Primary Examiner* — Catherine S Hibbert
(74) *Attorney, Agent, or Firm* — Parker Highlander PLLC

(57) ABSTRACT

Recombinant bacterial cells are provided that comprise a stable non-canonical amino acid translation pathway. In some aspects, the bacteria comprise nucleic acids encoding a non-canonical amino acid translation pathway (e.g., a tRNA for incorporation of a non-canonical amino acid, such as selenocysteine); a marker polypeptide that includes the non-canonical amino acid. Recombinant tRNA and selection marker coding sequences are likewise provided.

7 Claims, 9 Drawing Sheets

Specification includes a Sequence Listing.

SEQUENCE LISTING

```
<160> NUMBER OF SEQ ID NOS: 21

<210> SEQ ID NO 1
<211> LENGTH: 95
<212> TYPE: DNA
<213> ORGANISM: Artificial sequence
<220> FEATURE:
<223> OTHER INFORMATION: Synthetic oligonucleotide

<400> SEQUENCE: 1
ggaagatcgt cgtctccggt gaggcggctg gactctaaat ccagttgggg ccgccagcgg     60
tcccgggcag gttcgactcc tgtgatcttc cgcca                               95

<210> SEQ ID NO 2
<211> LENGTH: 95
<212> TYPE: DNA
<213> ORGANISM: Artificial sequence
<220> FEATURE:
<223> OTHER INFORMATION: Synthetic oligonucleotide

<400> SEQUENCE: 2
ggaagatggt cgtctccggt gaggcggctg gactctaaat ccagttgggg ccgccagcgg     60
tcccggtcag gttcgactcc ttgcatcttc cgcca                               95

<210> SEQ ID NO 3
<211> LENGTH: 95
<212> TYPE: DNA
<213> ORGANISM: Artificial sequence
<220> FEATURE:
<223> OTHER INFORMATION: Synthetic oligonucleotide

<400> SEQUENCE: 3
ggaagatggt cgtctccggt gaggcggctg gactctaaat ccagttgggg ccgccagcgg     60
tcccggcgag gttcgactcc tcgtatcttc cgcca                               95

<210> SEQ ID NO 4
<211> LENGTH: 90
<212> TYPE: DNA
<213> ORGANISM: Artificial sequence
<220> FEATURE:
<223> OTHER INFORMATION: Synthetic oligonucleotide

<400> SEQUENCE: 4
ggaagatgtg gccgagcggt tgaaggcacc ggtctctaaa accggcgacc cgaaagggtt     60
ccagagttcg aatctctgca tcttccgcca                                     90
```

-continued

```
<210> SEQ ID NO 5
<211> LENGTH: 13
<212> TYPE: DNA
<213> ORGANISM: Artificial sequence
<220> FEATURE:
<223> OTHER INFORMATION: Synthetic oligonucleotide

<400> SEQUENCE: 5
taggaggcag atc                                                            13

<210> SEQ ID NO 6
<211> LENGTH: 73
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (39)..(40)
<223> OTHER INFORMATION: n is a, c, g, or t
<220> FEATURE:
<221> NAME/KEY: misc_feature
<222> LOCATION: (54)..(56)
<223> OTHER INFORMATION: n is a, c, g, or t

<400> SEQUENCE: 6
tggactggtc tcccagttgg ggccgccagc ggtcccggnn aggttcgact cctnnnatct         60
tccgccaaaa tgc                                                            73

<210> SEQ ID NO 7
<211> LENGTH: 66
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (51)..(51)
<223> OTHER INFORMATION: n is a, c, g, or t

<400> SEQUENCE: 7
gctggcggtc tcaactggat ttagagtcca gccgcctcac cggagacgac natcttccgc         60
gcctcg                                                                    66

<210> SEQ ID NO 8
<211> LENGTH: 879
<212> TYPE: DNA
<213> ORGANISM: Artificial sequence
<220> FEATURE:
<223> OTHER INFORMATION: Synthetic oligonucleotide

<400> SEQUENCE: 8
atgtcactta atgtaaagca aagtagaata gccatcttgt ttagctcttg tttaatttca         60
atatcatttt tctcacaggc caatacgaag ggcattgatg agattaaaaa ccttgaaaca        120
gatttcaatg gcaggattgg tgtctacgct ttagacactg gctcgggtaa atcatttcg         180 tacagagcaa atgaacgatt tccattatgt agttctttta aaggtttttt agctgctgct        240
gtattaaaag gctctcaaga taatcgactt aatcttaatc agattgtgaa ttataataca        300
agaagtttag agttccattc acccatcaca actaaatata aagataatgg aatgtcatta        360
ggtgatatgg ctgctgctgc tttacaatat agcgacaatg gtgctactaa tattattctt        420
gaacgttata tcggtggtcc agagggtatg actaaattca tgcggtcgat tggagatgaa        480
gattttagac tcgatcgttg ggagttagat ctaaacacag ctattccagg cgatgagcgt        540
```

```
gacacatcta cacctgcagc agtagccaag agtctgaaaa cccttgctct gggtaacata      600
cttagtgaac atgaaaagga aacctatcag acatggttaa agggtaacac aaccggtgca      660
gcgcgtattc gtgctagcgt accaagcgat tgggtagttg gcgataaaac tggtagttgc      720
ggagcatacg gtacggcaaa tgattatgcg gtagtctggc caaagaaccg ggctcctctt      780
ataatttctg tatacacaac aaaaaacgaa aaagaagcca agcatgagga taaagtaatc      840
gcagaagctt caagaattgc aattgataac cttaaataa                              879
```

```
<210> SEQ ID NO 9
<211> LENGTH: 292
<212> TYPE: PRT
<213> ORGANISM: Artificial sequence
<220> FEATURE:
<223> OTHER INFORMATION: Synthetic polypeptide

<400> SEQUENCE: 9

Met Ser Leu Asn Val Lys Gln Ser Arg Ile Ala Ile Leu Phe Ser Ser
1               5                   10                  15

Cys Leu Ile Ser Ile Ser Phe Phe Ser Gln Ala Asn Thr Lys Gly Ile
                20                  25                  30

Asp Glu Ile Lys Asn Leu Glu Thr Asp Phe Asn Gly Arg Ile Gly Val
            35                  40                  45

Tyr Ala Leu Asp Thr Gly Ser Gly Lys Ser Phe Ser Tyr Arg Ala Asn
    50                  55                  60

Glu Arg Phe Pro Leu Cys Ser Ser Phe Lys Gly Phe Leu Ala Ala Ala
65                  70                  75                  80

Val Leu Lys Gly Ser Gln Asp Asn Arg Leu Asn Leu Asn Gln Ile Val
                85                  90                  95

Asn Tyr Asn Thr Arg Ser Leu Glu Phe His Ser Pro Ile Thr Thr Lys
            100                 105                 110

Tyr Lys Asp Asn Gly Met Ser Leu Gly Asp Met Ala Ala Ala Ala Leu
        115                 120                 125

Gln Tyr Ser Asp Asn Gly Ala Thr Asn Ile Ile Leu Glu Arg Tyr Ile
    130                 135                 140

Gly Gly Pro Glu Gly Met Thr Lys Phe Met Arg Ser Ile Gly Asp Glu
145                 150                 155                 160

Asp Phe Arg Leu Asp Arg Trp Glu Leu Asp Leu Asn Thr Ala Ile Pro
                165                 170                 175

Gly Asp Glu Arg Asp Thr Ser Thr Pro Ala Ala Val Ala Lys Ser Leu
            180                 185                 190

Lys Thr Leu Ala Leu Gly Asn Ile Leu Ser Glu His Glu Lys Glu Thr
        195                 200                 205

Tyr Gln Thr Trp Leu Lys Gly Asn Thr Thr Gly Ala Ala Arg Ile Arg
    210                 215                 220

Ala Ser Val Pro Ser Asp Trp Val Val Gly Asp Lys Thr Gly Ser Cys
225                 230                 235                 240

Gly Ala Tyr Gly Thr Ala Asn Asp Tyr Ala Val Val Trp Pro Lys Asn
                245                 250                 255

Arg Ala Pro Leu Ile Ile Ser Val Tyr Thr Thr Lys Asn Glu Lys Glu
            260                 265                 270

Ala Lys His Glu Asp Lys Val Ile Ala Glu Ala Ser Arg Ile Ala Ile
        275                 280                 285

Asp Asn Leu Lys
    290
```

<210> SEQ ID NO 10
<211> LENGTH: 516
<212> TYPE: DNA
<213> ORGANISM: Artificial sequence
<220> FEATURE:
<223> OTHER INFORMATION: Synthetic oligonucleotide

<400> SEQUENCE: 10

```
atgatcagtc tgattgcggc gttagcggtt gatcgcgtta tcggcatgga aaacgccatg      60
ccgtggaacc tgcctgccga tctcgcctgg tttaaacgca acaccttaaa taaaagtgtg     120
attatgggcc gccatacctg ggaatcaatc ggtcgtccgt tgccaggacg caaaaatatt     180
atcctcagca gtcaaccggg tacggacgat cgcgtaacgt gggtgaagtc ggtggatgaa     240
gccatcgcgg cgtgtggtga cgtaccagaa atcatggtga ttggcggcgg tcgcgtttat     300
gaacagttct tgccaaaagc gcaaaaactg tatctgacgc atatcgacgc agaagtggaa     360
ggcgacaccc atttcccgga ttacgagccg gatgactggg aatcggtatt cagcgaattc     420
cacgatgctg atgcgcagaa ctctcacagc tattgctttg agattctgga gcggcgggc     480
agctctgctt ggtctcaccc gcagttcgaa aaataa                               516
```

<210> SEQ ID NO 11
<211> LENGTH: 171
<212> TYPE: PRT
<213> ORGANISM: Artificial sequence
<220> FEATURE:
<223> OTHER INFORMATION: Synthetic polypeptide

<400> SEQUENCE: 11

Met Ile Ser Leu Ile Ala Ala Leu Ala Val Asp Arg Val Ile Gly Met
1               5                   10                  15

Glu Asn Ala Met Pro Trp Asn Leu Pro Ala Asp Leu Ala Trp Phe Lys
            20                  25                  30

Arg Asn Thr Leu Asn Lys Ser Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Gly Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Tyr Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Phe His Asp Ala Asp
    130                 135                 140

Ala Gln Asn Ser His Ser Tyr Cys Phe Glu Ile Leu Glu Arg Arg Gly
145                 150                 155                 160

Ser Ser Ala Trp Ser His Pro Gln Phe Glu Lys
            165                 170

<210> SEQ ID NO 12
<211> LENGTH: 516
<212> TYPE: DNA
<213> ORGANISM: Artificial sequence
<220> FEATURE:
<223> OTHER INFORMATION: Synthetic oligonucleotide

<400> SEQUENCE: 12

```
atgatcagtc tgattgcggc gttagcggtt gatcgcgtta tcggcatgga aaacgccatg      60
ccgtggaacc tgcctgccga tctcgcctgg tttaaacgca acaccttaaa taaataggtg     120
attatgggcc gccatacctg ggaatcaatc ggtcgtccgt tgccaggacg caaaaatatt     180
atcctcagca gtcaaccggg tacggacgat cgcgtaacgt gggtgaagtc ggtggatgaa     240
gccatcgcgg cgtgtggtga cgtaccagaa atcatggtga ttggcggcgg tcgcgtttat     300
gaacagttct tgccaaaagc gcaaaaactg tatctgacgc atatcgacgc agaagtggaa     360
ggcgacaccc atttcccgga ttacgagccg gatgactggg aatcggtatt cagcgaattc     420
cacgatgctg atgcgcagaa ctctcacagc tattgctttg agattctgga gcggcggggc     480
agctctgctt ggtctcaccc gcagttcgaa aaataa                                516
```

<210> SEQ ID NO 13
<211> LENGTH: 171
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (39)..(39)
<223> OTHER INFORMATION: Xaa = Selenocysteine (Sec)

<400> SEQUENCE: 13

```
Met Ile Ser Leu Ile Ala Ala Leu Ala Val Asp Arg Val Ile Gly Met
1               5                   10                  15

Glu Asn Ala Met Pro Trp Asn Leu Pro Ala Asp Leu Ala Trp Phe Lys
            20                  25                  30

Arg Asn Thr Leu Asn Lys Xaa Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Gly Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Tyr Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Cys Phe Glu Ile Leu Glu Arg Arg Gly
145                 150                 155                 160

Ser Ser Ala Trp Ser His Pro Gln Phe Glu Lys
                165                 170
```

<210> SEQ ID NO 14
<211> LENGTH: 465
<212> TYPE: DNA
<213> ORGANISM: Artificial sequence
<220> FEATURE:
<223> OTHER INFORMATION: Synthetic oligonucleotide

<400> SEQUENCE: 14

```
atgctgcgca agctggcggc agtgtccctg ctgtctctgc tgagcgcacc gctgctggcg      60
```

```
gccgagtgct ctgtggatat ccagggcaac gatcagatgc aattcaacac caacgcaatt    120
actgtagata atcttgtaa acagtttacc gttaacctgt ctcacccagg caacctgccg      180
aagaacgtta tgggccacaa ctgggtactg tctacggcag ctgatatgca gggtgttgtg    240
accgacggta tggcaagcgg cctggataag gattatctga aaccggatga ctcccgtgtt    300
atcgcacata cgaaactgat cggttccggt gaaaaagact ccgtcacttt tgacgttagc    360
aaactgaagg aaggcgaaca gtatatgttt ttcagtacct ccccgggcca ctctgccctg    420
atgaaaggca ctctgaccct gaagcatcac catcaccatc actaa                    465

<210> SEQ ID NO 15
<211> LENGTH: 154
<212> TYPE: PRT
<213> ORGANISM: Artificial sequence
<220> FEATURE:
<223> OTHER INFORMATION: Synthetic polypeptide

<400> SEQUENCE: 15

Met Leu Arg Lys Leu Ala Ala Val Ser Leu Leu Ser Leu Leu Ser Ala
1               5                   10                  15

Pro Leu Ala Ala Glu Cys Ser Val Asp Ile Gln Gly Asn Asp Gln
            20                  25                  30

Met Gln Phe Asn Thr Asn Ala Ile Thr Val Asp Lys Ser Cys Lys Gln
        35                  40                  45

Phe Thr Val Asn Leu Ser His Pro Gly Asn Leu Pro Lys Asn Val Met
    50                  55                  60

Gly His Asn Trp Val Leu Ser Thr Ala Ala Asp Met Gln Gly Val Val
65                  70                  75                  80

Thr Asp Gly Met Ala Ser Gly Leu Asp Lys Asp Tyr Leu Lys Pro Asp
                85                  90                  95

Asp Ser Arg Val Ile Ala His Thr Lys Leu Ile Gly Ser Gly Glu Lys
            100                 105                 110

Asp Ser Val Thr Phe Asp Val Ser Lys Leu Lys Glu Gly Glu Gln Tyr
        115                 120                 125

Met Phe Phe Ser Thr Phe Pro Gly His Ser Ala Leu Met Lys Gly Thr
    130                 135                 140

Leu Thr Leu Lys His His His His His His
145                 150

<210> SEQ ID NO 16
<211> LENGTH: 465
<212> TYPE: DNA
<213> ORGANISM: Artificial sequence
<220> FEATURE:
<223> OTHER INFORMATION: Synthetic oligonucleotide

<400> SEQUENCE: 16
atgctgcgca agctggcggc agtgtccctg ctgtctctgc tgagcgcacc gctgctggcg    60
gccgagtgct ctgtggatat ccagggcaac gatcagatgc aattcaacac caacgcaatt    120
actgtagata atcttgtaa acagtttacc gttaacctgt ctcacccagg caacctgccg      180
aagaacgtta tgggccacaa ctgggtactg tctacggcag ctgatatgca gggtgttgtg    240
accgacggta tggcaagcgg cctggataag gattatctga aaccggatga ctcccgtgtt    300
atcgcacata cgaaactgat cggttccggt gaaaaagact ccgtcacttt tgacgttagc    360
aaactgaagg aaggcgaaca gtatatgttt ttctagacct ccccgggcca ctctgccctg    420
atgaaaggca ctctgaccct gaagcatcac catcaccatc actaa                    465
```

<210> SEQ ID NO 17
<211> LENGTH: 154
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (132)..(132)
<223> OTHER INFORMATION: Xaa = Selenocysteine (Sec)

<400> SEQUENCE: 17

Met Leu Arg Lys Leu Ala Ala Val Ser Leu Leu Ser Leu Leu Ser Ala
1               5                   10                  15

Pro Leu Ala Ala Glu Cys Ser Val Asp Ile Gln Gly Asn Asp Gln
            20                  25                  30

Met Gln Phe Asn Thr Asn Ala Ile Thr Val Asp Lys Ser Cys Lys Gln
        35                  40                  45

Phe Thr Val Asn Leu Ser His Pro Gly Asn Leu Pro Lys Asn Val Met
    50                  55                  60

Gly His Asn Trp Val Leu Ser Thr Ala Ala Asp Met Gln Gly Val Val
65                  70                  75                  80

Thr Asp Gly Met Ala Ser Gly Leu Asp Lys Asp Tyr Leu Lys Pro Asp
                85                  90                  95

Asp Ser Arg Val Ile Ala His Thr Lys Leu Ile Gly Ser Gly Glu Lys
            100                 105                 110

Asp Ser Val Thr Phe Asp Val Ser Lys Leu Lys Glu Gly Glu Gln Tyr
        115                 120                 125

Met Phe Phe Xaa Thr Phe Pro Gly His Ser Ala Leu Met Lys Gly Thr
    130                 135                 140

Leu Thr Leu Lys His His His His His His
145                 150

<210> SEQ ID NO 18
<211> LENGTH: 95
<212> TYPE: DNA
<213> ORGANISM: Artificial sequence
<220> FEATURE:
<223> OTHER INFORMATION: Synthetic oligonucleotide

<400> SEQUENCE: 18
ggaagatggt cgtctccggt gaggcggctg gactctaaat ccagttgggg ccgccagcgg      60
tcccggtcag gttcgactcc ttgcatcttc cgcca                                95

<210> SEQ ID NO 19
<211> LENGTH: 95
<212> TYPE: DNA
<213> ORGANISM: Artificial sequence
<220> FEATURE:
<223> OTHER INFORMATION: Synthetic oligonucleotide

<400> SEQUENCE: 19
ggaagatcgt cgtctccggt gaggcggctg gactctaaat ccagttgggg ccgccagcgg      60
tcccggtcag gttcgactcc ttggatcttc cgcca                                95

<210> SEQ ID NO 20
<211> LENGTH: 94
<212> TYPE: DNA
<213> ORGANISM: Artificial sequence
<220> FEATURE:

-continued

```
<223> OTHER INFORMATION: Synthetic oligonucleotide

<400> SEQUENCE: 20
ggaagatcgt cgtctccggt gaggcggctg gactctaaat ccagttgggg ccgccagcgg      60
tcccggtaag gttcgactcc tatatcttcc gcca                                  94

<210> SEQ ID NO 21
<211> LENGTH: 94
<212> TYPE: RNA
<213> ORGANISM: Escherichia coli
<220> FEATURE:
<221> NAME/KEY: misc_feature
<222> LOCATION: (8)..(8)
<223> OTHER INFORMATION: n is a, c, g, or u
<220> FEATURE:
<221> NAME/KEY: misc_feature
<222> LOCATION: (67)..(68)
<223> OTHER INFORMATION: n is a, c, g, or u
<220> FEATURE:
<221> NAME/KEY: misc_feature
<222> LOCATION: (82)..(83)
<223> OTHER INFORMATION: n is a, c, g, or u

<400> SEQUENCE: 21
ggaagaungu cgucuccggu gaggcggcug gacucuaaau ccaguugggg ccgccagcgg      60
ucccggnnag guucgacucc unnaucuucc gcca                                  94
```

TRANSGENIC BACTERIA WITH EXPANDED AMINO ACID USAGE AND NUCLEIC ACID MOLECULES FOR USE IN THE SAME

This application claims the benefit of U.S. Provisional Patent Application No. 62/267,498, filed Dec. 15, 2015, the entirety of which is incorporated herein by reference.

The invention was made with government support under Grant No. CHE1402753 awarded by the National Science Foundation and Grant No. FA9550-10-1-0169 awarded by the Air Force Office of Scientific Research. The government has certain rights in the invention.

INCORPORATION OF SEQUENCE LISTING

The sequence listing that is contained in the file named "UTSBP1092US_ST25.txt", which is 17 KB (as measured in Microsoft Windows®) and was created on Dec. 12, 2016, is filed herewith by electronic submission and is incorporated by reference herein.

BACKGROUND OF THE INVENTION

1. Field of the Invention

The present invention relates generally to the field of molecular biology and protein engineering. More particularly, it concerns compositions and methods for producing and screening polypeptides including non-canonical amino acids.

2. Description of Related Art

Life on Earth has been shaped by the universal and almost static genetic code set early in evolutionary history. At the coding level, life's proteome has been confined to $^{20}$ canonical amino acids, as well as selenocysteine and pyrrolysine, two rare, naturally occurring non-canonical amino acids (NCAAs) with specialized incorporation pathways. Because of differences in the way in which tRNA molecules are charged by tRNA synthetases in different organisms, it is difficult to predict to what extent a tRNA charged with a non-canonical amino acid by an engineered tRNA synthetase will truly be orthogonal to the canonical set of tRNAs and tRNA synthetases in any given organism. There is frequently background charging of introduced tRNAs by native tRNA synthetases, and background charging of native tRNAs by introduced tRNA synthetases. These effects likely contribute to the rapid loss of any introduced system to allow for incorporation of a NCAA. Thus, to date, there remains a need for a stable system that provides incorporation of NCAAs and that can be applied to a broad range of host organisms.

SUMMARY OF THE INVENTION

In a first embodiment the invention provides a transgenic bacterial cell, said cell comprising heterologous nucleic acids encoding translation components for incorporation of at least a first non-canonical amino acid and a screenable or selectable marker polypeptide that exhibits enhanced activity when at least one position of the marker polypeptide is said first non-canonical amino acid. In some aspects the bacterial cell comprises a heterologous nucleic acid encoding a screenable marker that exhibits enhanced activity when at least one position of the marker polypeptide is said first non-canonical amino acid. In specific aspects, the screenable marker is a fluorescent or luminescent polypeptide.

In other aspects, the bacterial cell comprises a heterologous nucleic acid encoding a selectable marker that exhibits enhanced activity when at least one position of the marker polypeptide is said first non-canonical amino acid. In further aspects, the selectable marker is a polypeptide that provides antibiotic resistance. In particular aspects, the selectable marker is a beta-lactamase enzyme. In specific aspects, the beta-lactamase has least 85%, 90%, 91%, 92%, 93%, 94%, 95%, 96%, 97%, 98% or 99% identity to SEQ ID NO: 9 and wherein the positions corresponding to C69 and/or C238 are selenocysteine. In still further aspects, the positions corresponding to C69 and C238 are selenocysteine.

In some aspects, the bacterial cell is a Gram positive or a Gram negative bacterial cell. In some specific aspects, the bacterial cell is an *E. coli* cell. In other particular aspects, the bacterial cell is an *Enterobacter* or *Serratia* bacteria. In further aspects, the bacterial cell is an *Enterobacter cloacae* or *Serratia marcescens* bacterial cell.

In certain aspects, the translation components for incorporation of the first non-canonical amino acid comprise a nucleic acid encoding a tRNA and an aminoacyl-tRNA synthetase for the first non-canonical amino acid. In some aspects, the tRNA recognizes a UAG codon. In further aspects, the tRNA is at least 85%, 90%, 91%, 92%, 93%, 94%, 95%, 96%, 97%, 98% or 99% identical to SEQ ID NO: 18, SEQ ID NO: 19, SEQ ID NO: 20 or SEQ ID NO: 4. In specific aspects, the tRNA comprises SEQ ID NO: 18, SEQ ID NO: 19, SEQ ID NO: 20 or SEQ ID NO: 4.

In still further aspects, the translation components for incorporation of the first non-canonical amino acid further comprise a nucleic acid encoding an enzyme for synthesis for the first non-canonical amino acid. In a particular aspect, the non-canonical amino acid is selenocysteine. In other aspects, the cell comprises a nucleic acid encoding selA, selB and/or selC. In a specific aspect, the cell comprises a nucleic acid encoding selA. In some aspects, the bacterial cell comprises an inactivated or deleted prfA gene. In certain aspects, the cell has been engineered to lack endogenous Amber codons. In some particular aspects, the cell is or is derived from a *E. coli* C321.ΔA.

In a further embodiment the invention provides a population of bacterial cells in accordance with the embodiments and aspects described above. In certain aspects, the population comprises $1 \times 10^3$ to $1 \times 10^{12}$ bacterial cells.

In still a further embodiment, there is provided a method of producing a commercial polypeptide comprising at least a first non-canonical amino acid comprising (i) obtaining a bacterial cell according to the embodiments and an expression cassette encoding the commercial polypeptide; and (ii) incubating the bacterial cell in conditions that allow expression of the commercial polypeptide. In some aspects, the expression cassette encoding the commercial polypeptide is under the control of an inducible promoter. In certain aspects, the method further comprises isolating the expressed commercial polypeptide.

In yet still a further embodiment the invention provides a method of screening for a polypeptide having a desired activity comprising (i) obtaining a population of bacterial cells according to claim 1 and said cells encoding a library of candidate polypeptides, said polypeptides comprising at least a first non-canonical amino acid position; and (ii) screening the population of bacteria to identify a candidate polypeptide having the desired biological activity. In specific aspects, the population of bacterial cells comprises nucleic acid constructs encoding 100 to 10,000,000 different candidate polypeptides.

In still a further embodiment, there is provided a recombinant nucleic acid molecule, wherein the molecule encodes a tRNA that is at least 85%, 90%, 91%, 92%, 93%, 94%, 95%, 96%, 97%, 98% or 99% identical to SEQ ID NO: 18, SEQ ID NO: 19, or SEQ ID NO: 20 and comprising one or more of the following features: a G or C at a position corresponding to position 7; a T at a position corresponding to position 49; an A or C at a position corresponding to position 50; a T at a position corresponding to position 64; a G or A at a position corresponding to position 65; and/or a G, T or C at a position corresponding to position 66. In some particular aspects, the molecule encodes a tRNA comprising the sequence at least about 90% identical to SEQ ID NO: 18; and comprises one or more of the features listed above. In further specific aspects, the molecule comprises 2, 3, 4, 5 or 6 of the features listed above. In certain aspects, the molecule encodes a tRNA comprising the sequence at least about 90% identical to SEQ ID NO: 19 or SEQ ID NO: 20. In particular aspects, the molecule encodes a tRNA comprising the sequence of SEQ ID NO: 18, SEQ ID NO: 19, or SEQ ID NO: 20.

In yet still a further embodiment there is provided a recombinant polypeptide, encoding a beta-lactamase enzyme, said enzyme comprising a disulfide bond between two cysteine positions that is required for activity of the enzyme, where at least one of said two cysteine positions is substituted with a selenocysteine. In some aspects, both of said Cys positions are substituted with a selenocysteine. In further aspects, the beta-lactamase enzyme is SME-type beta-lactamase. For example, the beta-lactamase can comprises a sequence least 85%, 90%, 91%, 92%, 93%, 94%, 95%, 96%, 97%, 98% or 99% identical to SEQ ID NO: 9 and wherein the positions corresponding to C69 and/or C238 are selenocysteine. In certain aspects, the the positions corresponding to C69 and C238 are selenocysteine.

Further embodiments of the invention provide a recombinant nucleic acid molecule encoding the polypeptide according to the embodiments and aspects described above. In some aspects, the codons corresponding to the selenocysteine position(s) is a UAG codon. In other aspects, the sequence is at least about 85%, 90%, 91%, 92%, 93%, 94%, 95%, 96%, 97%, 98% or 99% identical to SEQ ID NO: 8.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.01%. Most preferred is a composition in which no amount of the specified component can be detected with standard analytical methods.

As used herein in the specification and claims, "a" or "an" may mean one or more. As used herein in the specification and claims, when used in conjunction with the word "comprising", the words "a" or "an" may mean one or more than one. As used herein, in the specification and claim, "another" or "a further" may mean at least a second or more.

As used herein in the specification and claims, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

I. The Present Embodiments

The use of non-canonical amino acids in proteins offers the possibility of polypeptides having greatly expanded functionality that could be exploited for wide range of applications. For example, by incorporation of selenocysteine into polypeptides it may be possible to develop enzymes having enhanced levels of stability or activity and to produce highly active therapeutic polypeptides. However, these approaches have, to date, been hampered by the inability to produce organisms that stability retain translation pathways that predictable and reliably incorporate selenocysteine into encoded polypeptides. Studies detailed herein demonstrate a stable system for selection of tRNA molecules that can incorporate selenocysteine and for production of polypeptides that incorporate selenocysteine positions. Importantly, this system can be easily moved from one organism to another with-out the need of re-engineering.

II. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Selection of tRNAs

Figures 1A, 1B, 1C:
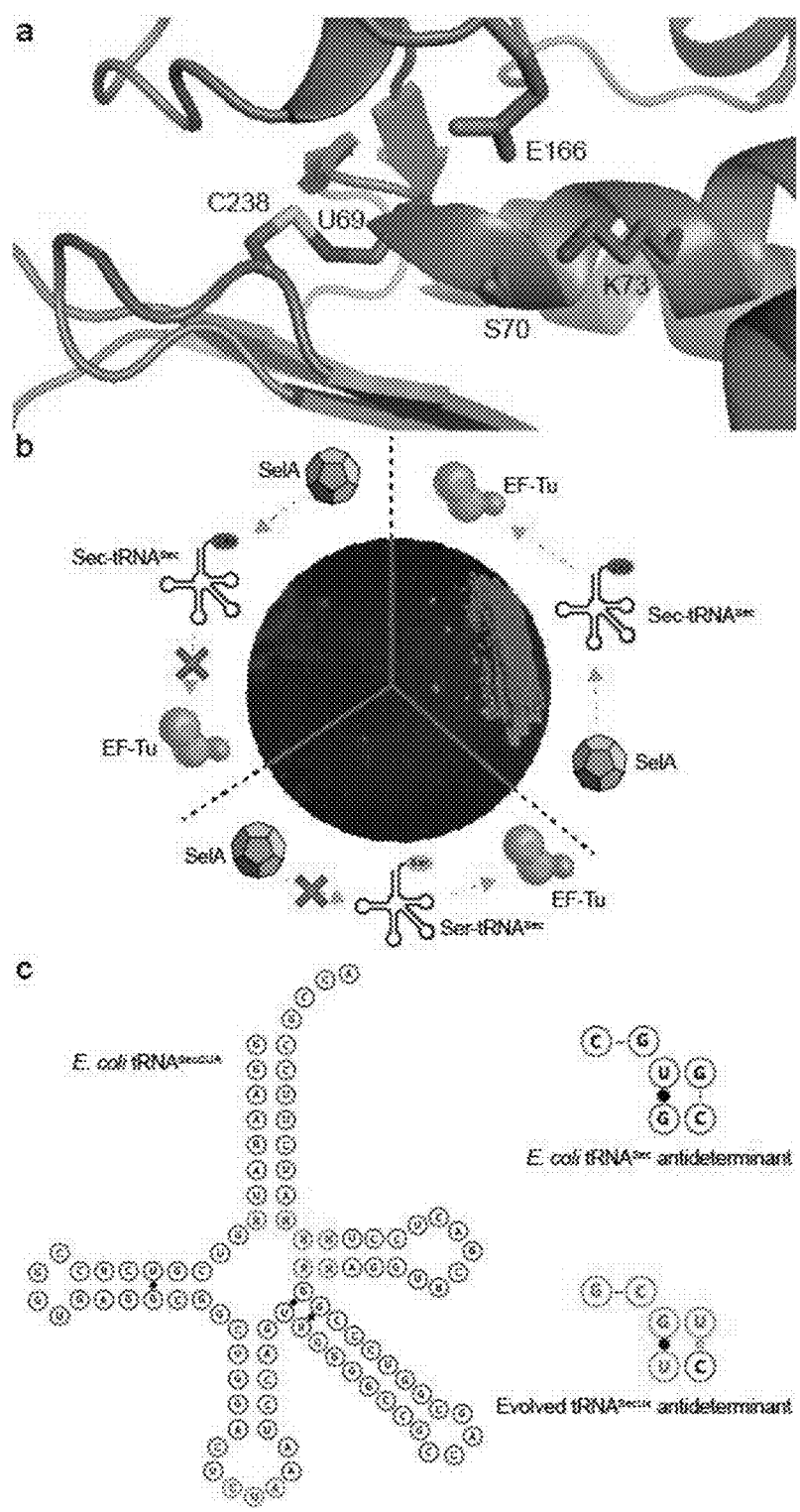
FIGS. 1a-1c—Selection of tRNAs capable of canonical incorporation of selenocysteine. (1a) Representation of the NMC-A β-lactamase from *Enterobacter cloacae* (PDB: 1BUE) showing the engineered selenyl-sulfhydryl bond between residues 69 and 238 and its proximity to the catalytic site. (1b) Validation of a β-lactamase reporter capable of discriminating serine from selenocysteine. Three NMC-A variants, C69X (TAG), C69 and C69S (clockwise from left), were constructed to determine the threshold for selection (<50 µg·mL$^{-1}$). These approximate the following outcomes during selection: Termination at the amber stop codon due to inefficient interaction with EF-Tu, impaired interaction with SelA promoting incorporation of serine, and efficient interactions with both SelA and EF-Tu resulting in incorporation of selenocysteine. (1c) Representation of *E. coli* tRNA$^{SecCUA}$ and the evolved antideterminant sequence (SEQ ID NO: 21). The antideterminant library is shown expanded on the right and the CUA anticodon is shown at the bottom of the figure.

A method of genetic selection capable of discriminating different levels of selenocysteine incorporation was developed. To specifically 'addict' a reporter protein to selenocysteine rather than serine, the NMC-A β-lactamase from *Enterobacter cloacae* was used. This enzyme has high sequence similarity to the SME-1 β-lactamase from *Serratia marcescens*, an enzyme that has previously been shown to require a disulfide bond adjacent to the active site serine residue for activity, but that confers a significant fitness cost on *E. coli*.[16] First, a C69S mutant was constructed of NMC-A, which failed to confer resistance to ampicillin (MIC<50 μg·mL:$^{-1}$), indicating that the disulfide bond was essential for activity (FIG. 1b). Then cysteine 69 was replaced with an amber stop codon (X69; FIG. 1a) for library selection, hypothesizing that the incorporation of selenocysteine and the formation of a selenyl-sulfhydryl bond would restore activity. (Swarén et al., 1998)

To eliminate any crosstalk between the tRNA$^{Sec}$ library and the endogenous selenocysteine incorporation machinery, the selA, selB and selC genes (encoding SelA, SelB and tRNA$^{Sec}$ respectively) were deleted from *E. coli* DH10B (designated DHΔabc). Cells containing the reporter plasmid pNMC-A C69X and the accessory plasmid pRSF-eSelA (expressing SelA) were transformed with plasmid pMB1-ZU containing the tRNA$^{Sec}$ antideterminant library. Transformants were plated on media containing a gradient of ampicillin concentrations for selection of mutants capable of selenocysteine-specific suppression. The single colonies that arose covered a range of ampicillin concentrations. Some 12 colonies from each plate were sequenced and revealed three distinct tRNA$^{Sec}$ mutants:

G$_7$-C$_{66}$:U$_{49}$-G$_{65}$:C$_{50}$-U$_{64}$
(GGAAGATG$_7$GTCGTCTCCGGTGAGGCGGCTGGACTCTAAATCCAG

TTGGGGCCGCCAGCGGTCCCGGT$_{49}$C$_{50}$AGGTTCGACTCCTT$_{64}$G$_{65}$C$_{66}$

ATCTTCCGCCA; SEQ ID NO: 18),

C$_7$-G$_{66}$:U$_{49}$-G$_{65}$:C$_{50}$-U$_{64}$
(GGAAGATC$_7$GTCGTCTCCGGTGAGGCGGCTGGACTCTAAATCCAGT

TGGGGCCGCCAGCGGTCCCGGT$_{49}$C$_{50}$AGGTTCGACTCCTT$_{64}$G$_{65}$G$_{66}$

ATCTTCCGCCA; SEQ ID NO: 19)
and

C$_7$-U$_{66}$:U$_{49}$-A$_{65}$:A$_{50}$-A$_{64}$
(GGAAGATC$_7$GTCGTCTCCGGTGAGGCGGCTGGACTCTAAATCCAGT

TGGGGCCGCCAGCGGTCCCGGT$_{49}$A$_{50}$AGGTTCGACTCCTA$_{65}$T$_{66}$

ATCTTCCGCCA; SEQ ID NO: 20)

(where underlined bases represent changes from the parental antideterminant sequence). Of these tRNA$^{Sec}$ variants, only G$_7$-C$_{66}$:U$_{49}$-G$_{65}$:C$_{50}$-U$_{64}$ was detected at the two highest ampicillin concentration (200 and 250 μg·ml$^{-1}$).

Figures 2A, 2B:
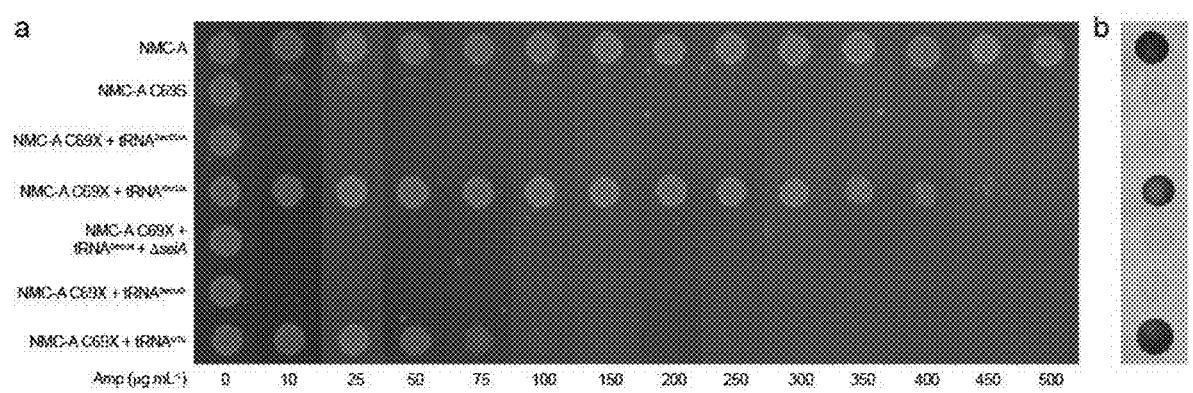
FIGS. 2a-2b—Activity of tRNA$^{Sec}$ variants in canonical translation. (2a) NMC-A β-lactamase reporter assay. From top row: Wild type NMC-A β-lactamase, NMC-A C69S, NMC-A C69X with tRNA$^{SecCUA}$, NMC-A C69X with tRNA$^{SecUx}$, NMC-A C69X with tRNA$^{SecUx}$ and inactive SelA, NMC-A C69X with tRNA$^{SecUG}$ containing a strong EF-Tu binding sequence and NMC-A C69X with tRNA$^{UTu}$. The observed dynamic range of the selection exceeds 20 fold. (2b) Reduction of benzyl viologen by *E. coli* formate dehydrogenase H confirms selenocysteine is incorporated by the tRNA$^{SecUx}$. Plate layout is identical to (2a) with FdhH, FdhH U140S and FdhH U140TAG reporters replacing the NMC-A reporter.
Figures 3A, 3B, 3C, 3D:
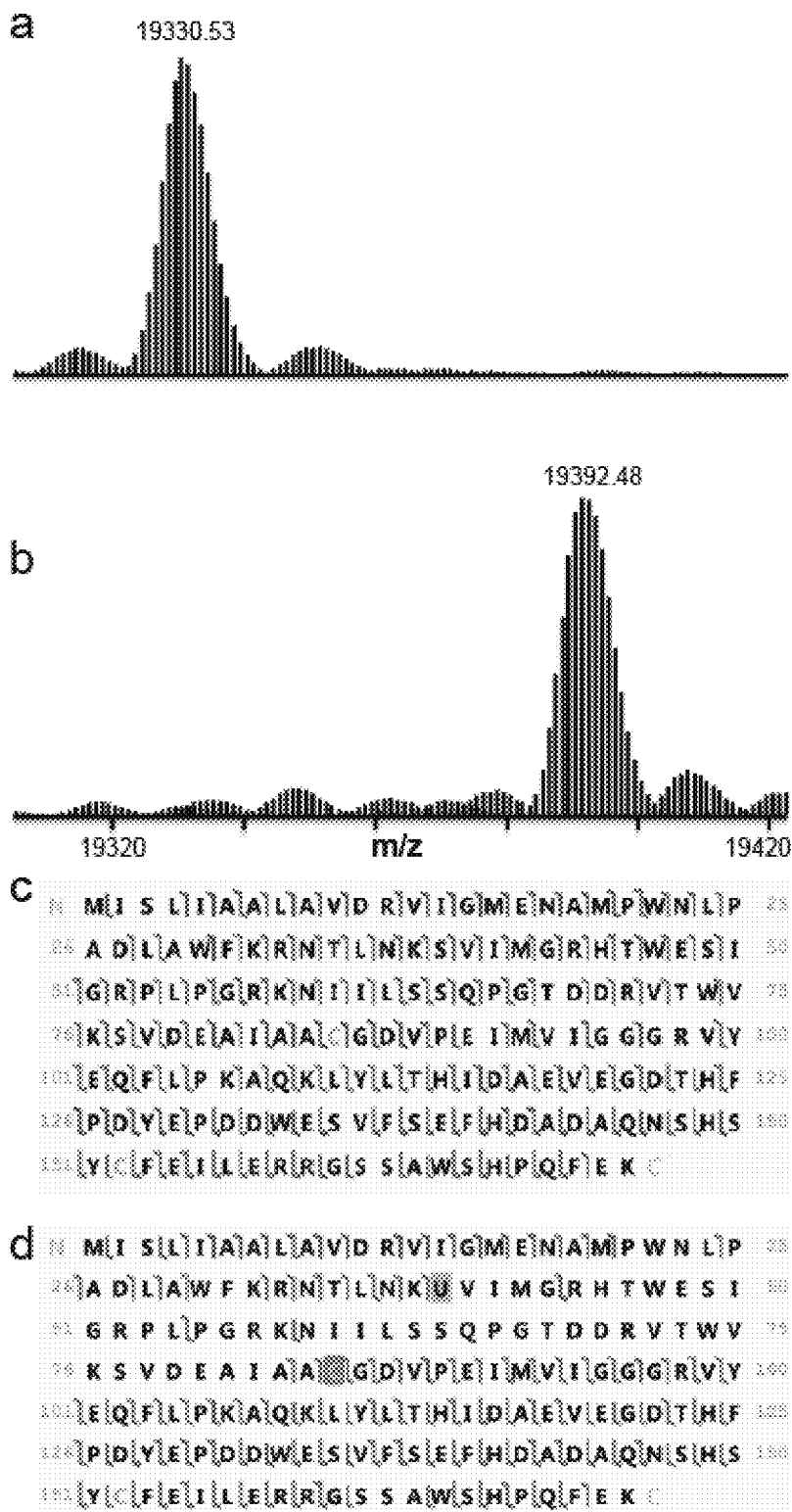
FIGS. 3a-3d—Intact mass and 193 nm UVPD results are shown for DHFR and seleno-DHFR produced using tRNA-$^{SecUx}$. For the sequence information shown, disulfide-bound cysteines are shaded in gray as are selenocysteine positions. When selenocysteine is located at position 39, it forms a selenyl-sulfhydryl bond with the cysteine at position 85. The slash marks represent the cleavage sites that lead to different N-terminal and C-terminal ions. (3a) Expanded region of the deconvoluted mass spectrum of DHFR with serine at position 39 (expected average mass m/z 19331.72). (3b) Expanded region of the deconvoluted mass spectrum of DHFR with selenocysteine incorporated at position 39 using tRNA$^{SecUx}$ (expected average mass m/z 19392.66). (3c) UVPD fragmentation map of DHFR P39S obtained for the 20+ charge state (SEQ ID NO: 11, encoded by a DNA sequence of SEQ ID NO: 10). (3d) UVPD fragmentation map of DHFR with selenocysteine at position 39, 18+ charge state (SEQ ID NO: 13, encoded by a DNA sequence of SEQ ID NO: 12).

The tRNA$^{Sec}$ variant containing the G$_7$-C$_{66}$:U$_{49}$-G$_{65}$:C$_{50}$-U$_{64}$ (SEQ ID NO: 18) antideterminant sequence was designated tRNA$^{SecUx}$ and was compared with the previously designed chimera (tRNA$^{UTu}$) and with a tRNA$^{Sec}$ derivative designed to have an antideterminant region that should tightly bind EF-Tu (tRNA$^{UG}$; FIG. 2a). The parental tRNA-$^{Sec}$ containing a CUA anticodon and tRNA$^{UG}$ failed to produce active β-lactamase. The hybrid tRNA$^{UTu}$ incorporated selenocysteine and could grow on 75βg·mL$^{-1}$. In contrast, expression of tRNA$^{SecUx}$ resulted in significantly higher β-lactamase activity (up to 400 βg·ml$^{-1}$), but only when co-expressed with SelA, confirming activity was selenocysteine dependent. To further confirm tRNA$^{SecUx}$ incorporated selenocysteine in response to amber stop codons, a standard colorimetric assay was employed based on the activity of the endogenous *E. coli* selenoprotein formate dehydrogenase H (FdhH) (FIG. 2b). FdhH is expressed under anaerobic conditions and catalyses the oxidation of formate to produce CO$_2$ with the concomitant reduction of the electron acceptor benzyl viologen resulting in the development of a deep purple color.[18] Formate oxidation by FdhH is strictly dependent on the selenocysteine residue at position 140; the mutant FdhH U140S was completely inactive. Only tRNA$^{SecUx}$ and tRNA$^{UTu}$ when co-expressed with SelA produced active FdhH.

The selected tRNA contained a non-standard sequence in the junction that normally interacts with EF-Tu. Given that neither the base of the acceptor stem nor the adjoining T-arm base pairs are believed to play a role in the interaction between tRNA$^{Sec}$ and SelA, the results suggest that the selected U:C leads to stronger binding to EF-Tu than the wild-type tRNA$^{Sec}$ sequence (Itoh et al., 2013). The unusual C$_{50}$-U$_{64}$ base pair is not predicted to bind strongly to EF-Tu based on models developed for canonical tRNAs (Schrader et al., 2011), and expression of a hybrid tRNA$^{UG}$ containing the strong EF-Tu binding region from the major *E. coli* tRNA$^{Gly}$ did not lead to the production of active β-lactamase, suggesting that the non-standard sequence was functionally important. Thus, it is possible that portions of the engineered tRNA$^{Sec}$ bind to EF-Tu differently than do canonical tRNAs, which would not necessarily be surprising given that tRNA$^{Sec}$ normally interacts with SelB (Li and Yarus, 1992).

Figure 4:
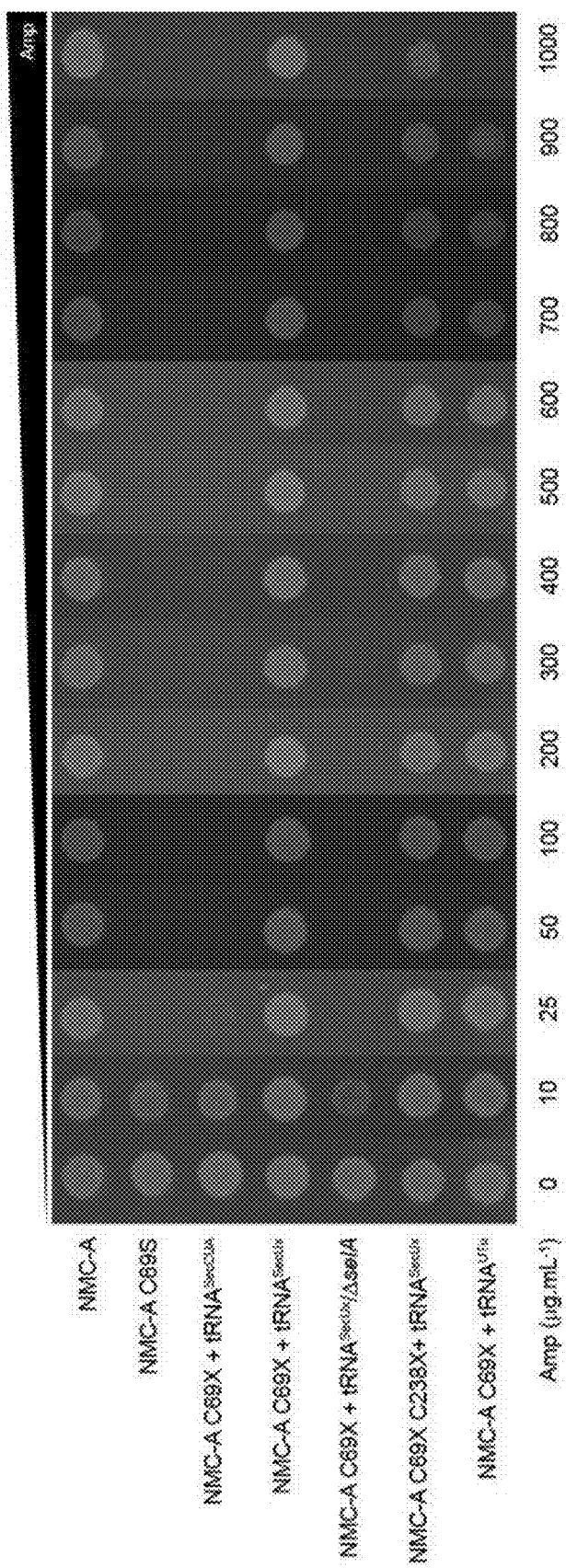
FIG. 4—Activity of tRNA$^{SecUx}$ in canon translation in an *E. coli* strain lacking release factor 1. NMC-A β-lactamase reporter assay. From top row: Wild type NMC-A β-lactamase, NMC-A C69S, NMC-A C69X with tRNA$^{SecCUA}$, NMC-A C69X with tRNA$^{SecUx}$, NMC-A C69X with tRNA$^{SecUx}$ and inactive SelA, NMC-A C69X C238X with tRNA$^{SecUx}$ and NMC-A C69X with tRNA$^{UTu}$. Use of the prfA minus *E. coli* strain dramatically enhances selenocysteine incorporation and β-lactamase activity. Incorporation of selenocysteine at both positions 69 and 238 also results in strong β-lactamase activity indicating efficient formation of a diselenide bond.
Figures 5A, 5B, 5C, 5D, 5E:
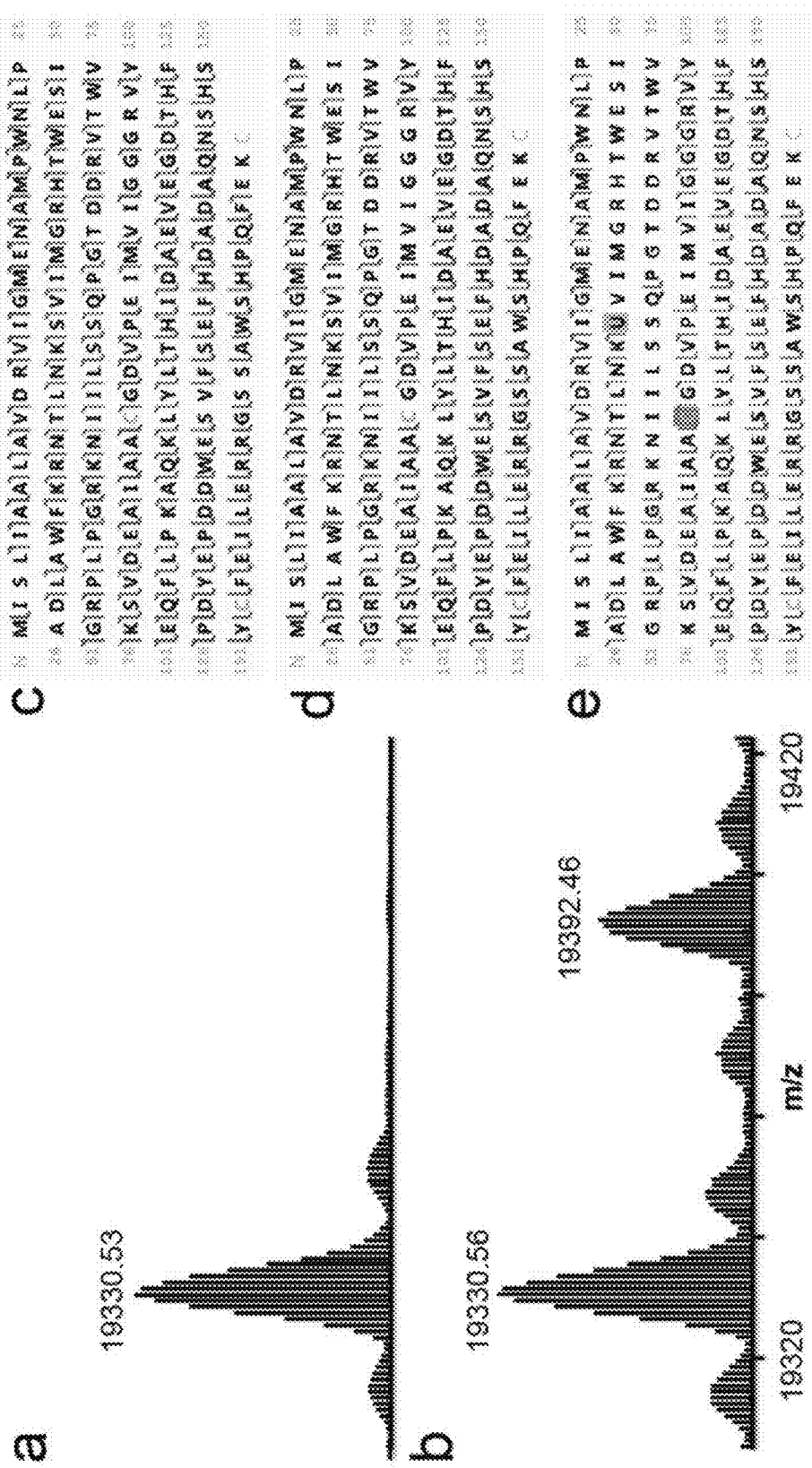
FIGS. 5a-5e—Intact mass and 193 nm UVPD results are shown for recombinant DHFR and seleno-DHFR produced using tRNA$^{UTu}$. For the sequences shown on the right, covalently bonded cysteine residues are shaded in gray as is the selenocysteine. When selenocysteine is located at position 39, it forms a selenyl-sulfhydryl bond with cysteine at position 85. The slash marks represent the cleavage sites that lead to different N-terminal and C-terminal ions. (a) Expanded region of the deconvoluted mass spectrum of DHFR with serine at position 39 (expected average mass m/z 19331.72). (b) Expanded region of the deconvoluted mass spectrum of seleno-DHFR with selenocysteine incorporated at position 39 produced using tRNA$^{UTu}$ (expected average mass m/z 19392.66). (c) UVPD fragmentation map of DHFR obtained for the 20+ charge state (SEQ ID NO: 11, encoded by a DNA sequence of SEQ ID NO: 10). (d) and (e) UVPD fragmentation maps of DHFR with serine or selenocysteine at position 39, 20+ charge state (d, depicts SEQ ID NO: 11, e, depicts SEQ ID NO: 13). Due to their similar masses, DHFR containing serine and DHFR containing selenocysteine were co-isolated (20+ charge state) for UVPD, and thus (d) shows the fragment map corresponding to serine-containing DHFR and (e) shows the fragment map corresponding to selenocysteine-containing DHFR.
Figures 6A, 6B, 6C, 6D, 6E:
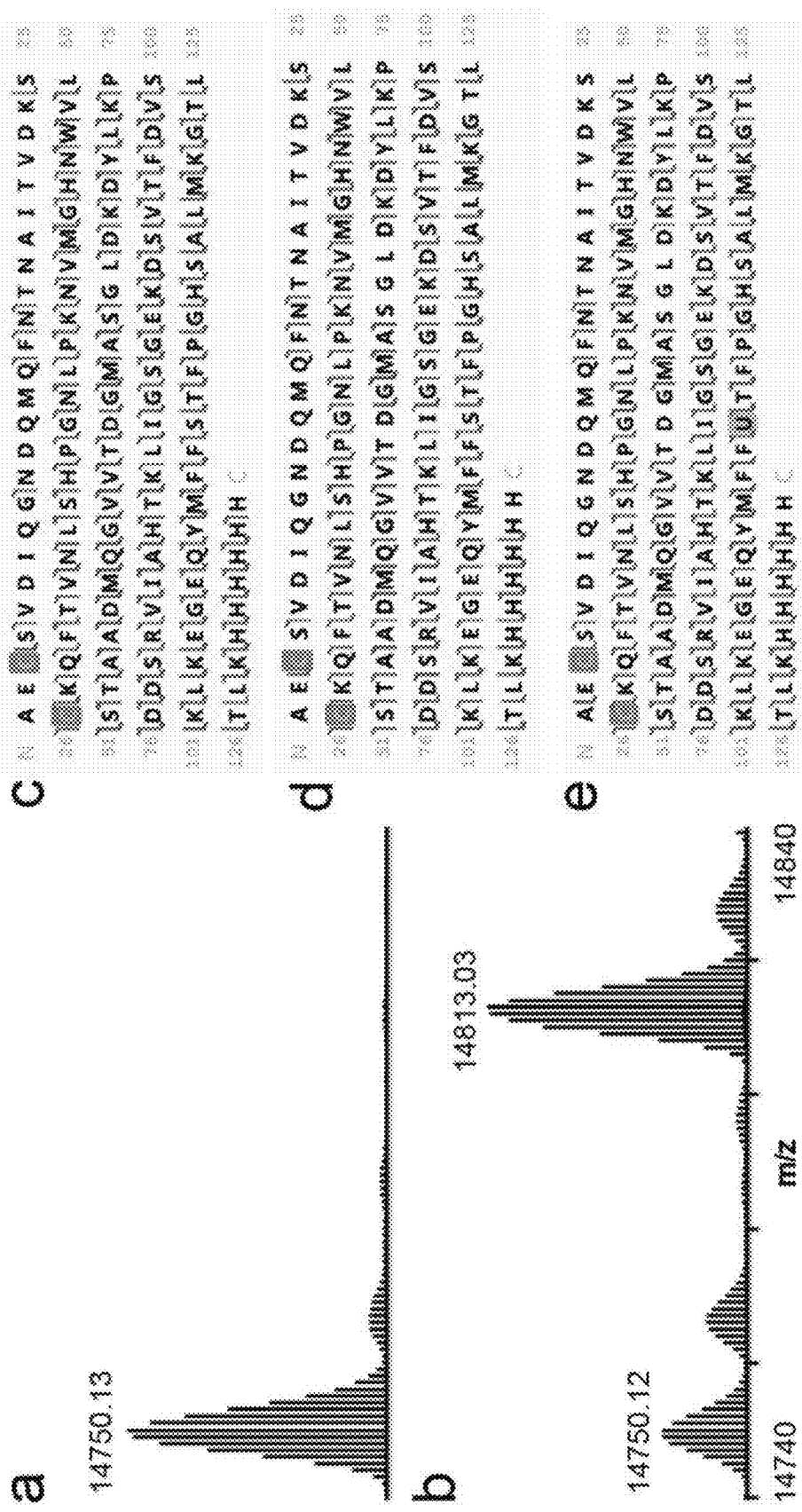
FIGS. 6a-6e—Intact mass and 193 nm UVPD results for recombinant azurin and seleno-azurin produced using tRNA$^{SecUx}$. For the sequences shown on the right, disulfide-bound cysteine residues are shaded in gray as are selenocysteine positions. The slash marks represent the cleavage sites that lead to different N-terminal and C-terminal ions. (a) Expanded region of the deconvoluted mass spectrum of azurin with serine at position 112 (expected average mass m/z 14750.54). (b) Expanded region of the deconvoluted mass spectrum of azurin with selenocysteine incorporated at position 112 produced using tRNA$^{SecUx}$ (expected average mass m/z 14813.50). (c) UVPD fragmentation map of azurin obtained for the 17+ charge state (SEQ ID NO: 15, encoded by the DNA of SEQ ID NO: 14). (d) and (e) UVPD fragmentation maps of azurin produced using tRNA$^{SecUx}$, (d, depicts SEQ ID NO: 11, e, is SEQ ID NO: 17, encoded by the DNA of SEQ ID NO: 17). Due to their similar masses, azurin and seleno-azurin were co-isolated (17+ charge state) for UVPD fragmentation where (d) shows the fragment map corresponding to serine-containing azurin (serine at position 112) and (e) shows the fragment map corresponding to seleno-azurin (selenocysteine at position 112).

The development of engineered *E. coli* strains lacking the prfA gene encoding release factor 1 (RF1) has allowed efficient incorporation of a range of unnatural amino acids (Mukai et al., 2010; Lajoie et al., 2013), and the development of the genome-engineered 'Amberless' *E. coli* C321.ΔA (Lajoie et al., 2013) provided an excellent opportunity to determine whether proteins that efficiently incorporated selenocysteine could be expressed. The selA, selB and selC genes were deleted in C321.ΔA (designated strain RTΔA), and cells were transformed with the amber-containing NMC-A reporter and accessory plasmids (FIG. 4). β-lactamase activity was dramatically increased in RF1-deficient cells compared to prfA$^+$ DHΔabc cells that still contain RF1. In addition, in a RF1-deficient background tRNA$^{SecUx}$ could now support the formation of a functional diselenide bond (via amber-mediated incorporation of two selenocysteine residues, U69 and U238; FIG. 4).

Figures 7A, 7B, 7C:
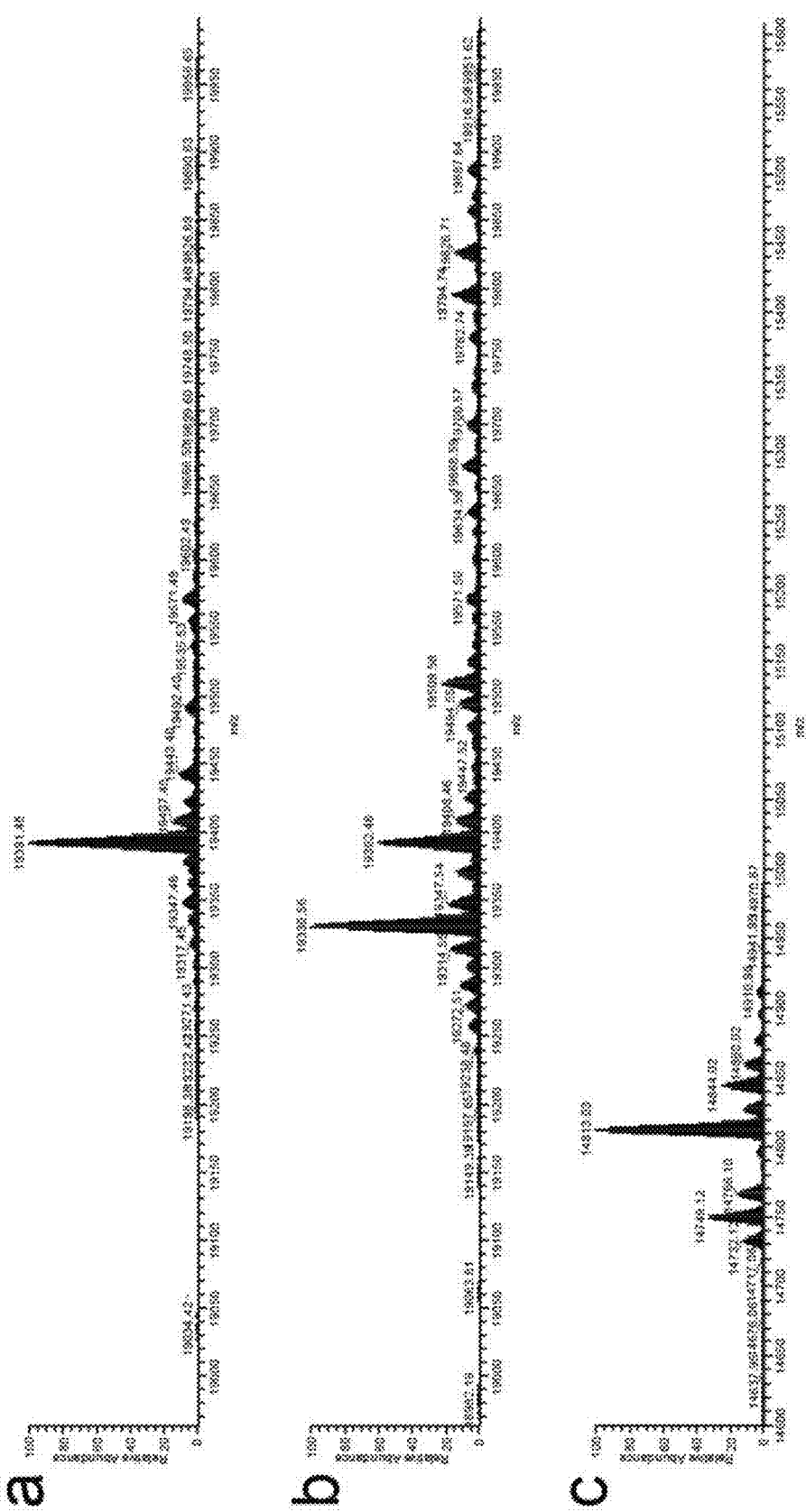
FIGS. 7a-7c—Deconvoluted full scan mass spectra for seleno-DHFR and seleno-azurin. All protein variants observable for each selenoprotein are shown in the above deconvoluted spectra. (a) Seleno-DHFR produced using tRNA$^{SecUx}$. (b) Seleno-DHFR produced using tRNA$^{UTu}$. (c) Seleno-azurin produced using tRNA$^{SecUx}$.
Figures 8A, 8B:
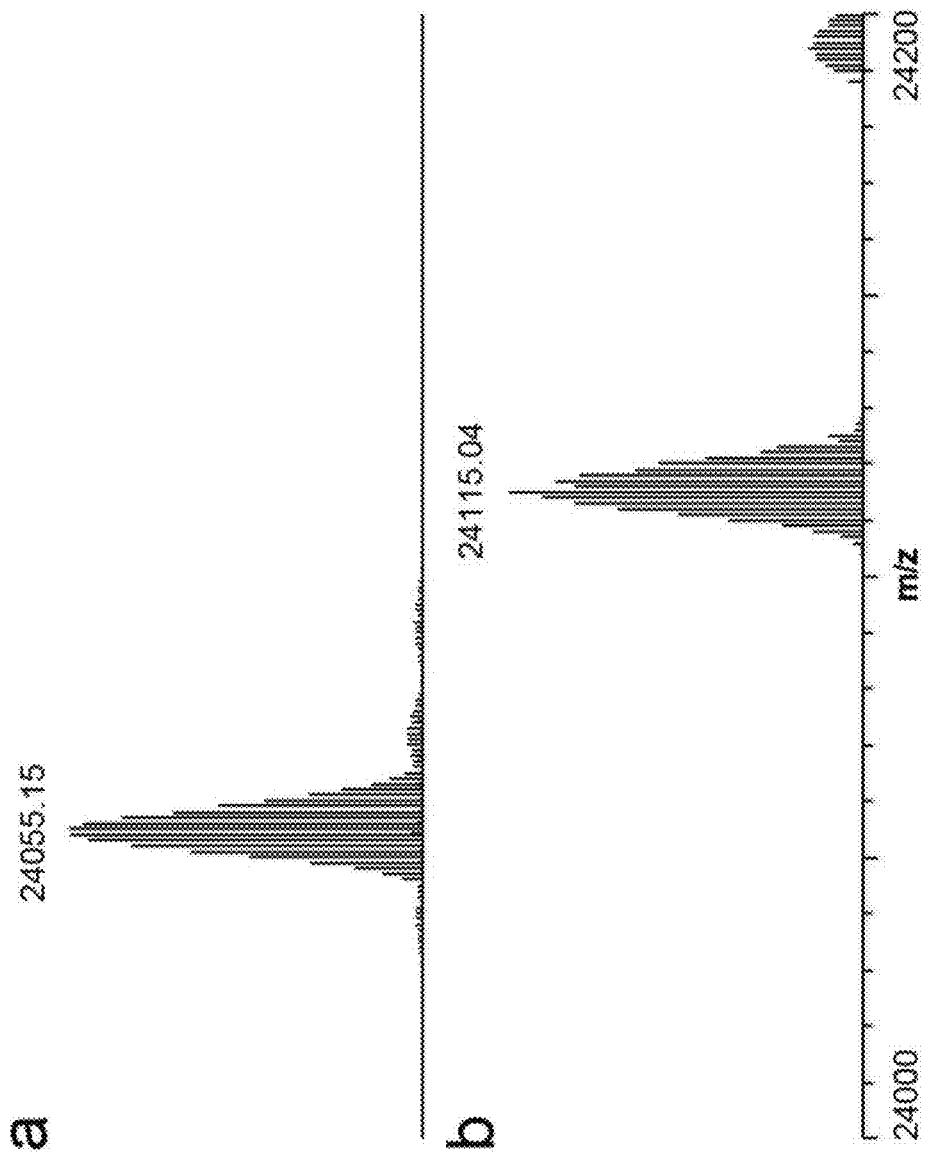
FIGS. 8a-8b—Intact masses for GPx-1 U49S and GPx-1 U49. (a) Expanded region of the deconvoluted mass spectrum of GPx-1 with serine at codon 49 (expected average mass m/z 24055.06) (b) Expanded region of the deconvoluted mass spectrum of GPx-1 with selenocysteine at codon 49 (expected average mass m/z 24116.21).
Figure 9:
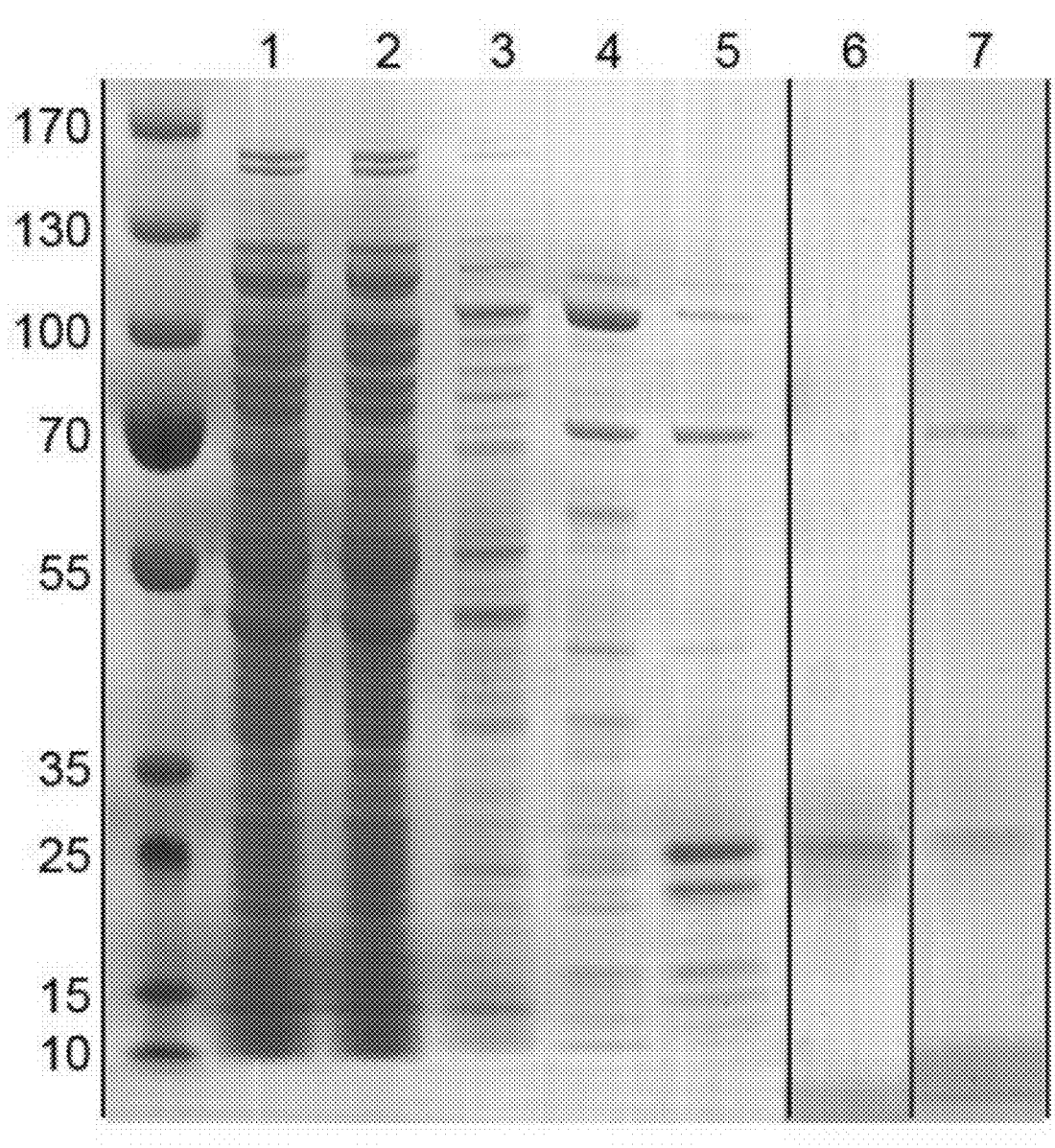
FIG. 9—Purification of GPx-1 U49. Combined SDS PAGE gel showing purification of recombinant GPx-1 U49 containing selenocysteine. Lanes 1-7 represent cell lysate, Ni-NTA waste fraction, 20 mM imidazole fraction, 50 mM imidazole fraction, 500 mM imidazole elution, Q sepharose unbound fraction and Q sepharose 750 mM NaCl fraction respectively. Lanes 1-5 and 6-7 represent different gels. The expected MW of the GPx-1 U49 monomer is 24 kDa.

To further enhance the efficiency of selenocysteine incorporation, a number of steps were taken to improve the levels of Sec-tRNA$^{Sec}$ relative to Ser-tRNA$^{Sec}$, including increasing the level of SelA, decreasing the gene dose of tRNA$^{SecUx}$, and co-expressing a phosphoseryl-tRNA$^{Sec}$ kinase (see Example 2 below). To monitor the efficiency of selenocysteine incorporation and demonstrate the possibilities for protein engineering, *E. coli* dihydrofolate reductase (DHFR) was produced containing an engineered non-essential selenyl-sulfhydryl bond (Villafranca et al., 1987). Top down mass spectrometry showed close to 100% selenocysteine incorporation with no detectable background corresponding to DHFR containing serine (FIG. 3a-d). The rationally designed tRNA$^{UTu}$ chimera was also observed to incorporate selenocysteine in DHFR containing a P39X substitution, but resulted in a much lower level of selenocysteine incorporation (38%) and significant serine incorporation (62%) (FIG. 4). No masses corresponding to the incorporation of other canonical amino acids were observed in the mass spectra (FIGS. 7a-7c). In order to further validate selenocysteine incorporation, the *Pseudomonas aeruginosa* metalloprotein azurin was also expressed with its essential cysteine (C112) replaced by selenocysteine and the human selenoprotein cellular glutathione peroxidase (GPx-1) (FIGS. 6a-6e and 8a-8b). For azurin, this chemical change had previously proven possible only through expressed protein ligation,[22] the essential cysteine could now be biologically replaced with selenocysteine with good efficiency as measured by mass spectrometry of the intact protein.

Example 2—Methods

Strain Construction

The selAB and selC genes were deleted from *E. coli* DH10B using the lambda Red system adapted from Datsenko and Wanner (2000). Antibiotic resistance cassettes were excised using FLP recombinase to generate strain DHΔabc. Deletion of the entire fdhF open reading frame yielded strain DHΔabcF.

E. coli C321βA was obtained from Addgene. A ~12 kb genomic region containing lambda phage genes and the TEM-1 β-lactamase inserted during development of the strain (Lajoie et al., 2013) was removed to facilitate stable growth at 37° C. and restore sensitivity to β-lactam antibiotics. Subsequent deletion of the selAB and selC genes and excision of antibiotic resistance cassettes generated strain RTΔA. To improve recombinant protein production, deletion of the lon gene encoding the Lon protease and truncation of the rne gene to remove 477 amino acids from the C-terminal of RNase E was performed, resulting in RTΔA.2.

Reporter Plasmids

All reporter plasmids were derived from pcat-pheS (Thyer et al., 2013). A 3281 bp fragment from pcat-pheS containing the 15A origin of replication and tetA gene conferring tetracycline resistance was ligated to an 1158 bp synthetic DNA fragment containing the $bla_{SME-1}$ gene from Serratia marcescens encoding the SME-1 β-lactamase flanked by endogenous promoter and terminator sequences. This plasmid (pSME-1) was found to be highly toxic to E. coli host cells and was poorly maintained. Replacement of the $bla_{SME-1}$ open reading frame with $bla_{NMC-A}$ from Enterobacter cloacae encoding the NMC-A β-lactamase which shares nearly 70% sequence identity (Majiduddin and Palzkill 2003) with SME-1 generated plasmid pNMC-A which did not exhibit any toxicity. pNMC-A variants with serine or amber codons at residues 69 and 238 were generated by QuikChange site directed mutagenesis.

p15A-fdhF was constructed by ligating the pcat-pheS derived fragment with a 2886 bp fragment amplified from E. coli DH10B genomic DNA containing the fdhF gene, the endogenous promoter and terminator sequences and the upstream formate response elements (Schlensog et al., 1994). U140S and U140TAG variants were generated by QuikChange site directed mutagenesis.

Accessory Plasmids

The RSF1030 origin of replication and kan cassette were amplified by PCR as a 1563 bp fragment from pRSFDuet-1 (Novagen). A 1562 bp fragment containing the E. coli selA gene and 5' region covering the endogenous promoter (Sawers et al., 1991) was amplified from E. coli DH10B genomic DNA. Assembly of the two fragments yielded plasmid pRSF-SelA. Replacement of the endogenous weakly active promoter with the strong constitutively active EM7 promoter and a canonical Shine-Dalgarno sequence resulted in plasmid pRSF-eSelA. SelA expression plasmids were validated by complementing E. coli DH10B deleted for selA (DHΔa) measured by benzyl viologen assay. Compared to pRSF-SelA, pRSF-eSelA induced a strong color change and this variant was used for all further experiments.

pRSF-U-eSelA was constructed by the addition of NotI and NcoI restriction sites between the RSF1030 origin and selA promoter and subcloning of the NotI/NcoI fragment containing the selC gene from pMB1-ZU. pRSF-U-eSelA variants containing mutant $tRNA^{Sec}$ genes were constructed by enzymatic inverse PCR. $tRNA^{Sec}$ sequences are shown in Table 1. Plasmid pRSF-U-ΔSelA containing a truncated selA gene was generated by QuikChange site directed mutagenesis introducing TGA and TAA stop codons at positions 167 and 168 respectively.

TABLE 1

Variant tRNAsec sequences. Shading represents the anticodon and underline represents the antideterminant region.

| Variant | tRNA Sequence |
|---|---|
| $tRNA^{SecCUA}$ (SEQ ID NO: 1) | GGAAGATCGTCGTCTCCGGTGAGGCGGCTGGACTCTAAATCCAGTTGG GGCCGCCAGCGGTCCCGGGCCAGGTTCGACTCCTGTGATCTTCCGCCA |
| $tRNA^{SecUx}$ (SEQ ID NO: 2) | GGAAGATGGTCGTCTCCGGTGAGGCGGCTGGACTCTAAATCCAGTTGG GGCCGCCAGCGGTCCCGGTCAGGTTCGACTCCTTGCATCTTCCGCCA |
| $tRNA^{SecUG}$ (SEQ ID NO: 3) | GGAAGATGGTCGTCTCCGGTGAGGCGGCTGGACTCTAAATCCAGTTGG GGCCGCCAGCGGTCCCGGCGAGGTTCGACTCCTCGTATCTTCCGCCA |
| $tRNA^{UTu}$ (SEQ ID NO: 4) | GGAAGATGTGGCCGAGCGGTTGAAGGCACCGGTCTCTAAAACCGGCGA CCCGAAAGGGTTCCAGAGTTCGAATCTCTGCATCTTCCGCCA |

Plasmid pRSF-eSelAK for constitutive expression of both SelA and PSTK was constructed by insertion of a synthetic DNA fragment between the selA gene and the kan cassette adding a luxI terminator 3' of selA and the Methanocaldococcus jannaschii pstK gene encoding O-phosphoseryl-$tRNA^{Sec}$ kinase (PSTK) codon optimized for expression in E. coli and flanked by the EM7 promoter and luxI terminator.

Expression Plasmids

All expression plasmids were derived from pRST.11 (Hughes and Ellington, 2010). For pDHFR-P39X-AU, the wrsI gene was replaced with an operon controlled by the constitutive EM7 promoter containing the E. coli folA gene (amplified from DH10B genomic DNA) encoding dihydrofolate reductase with a C-terminal Strep II tag joined by a serine/alanine linker and the selA gene separated by the sequence TAGGAGGCAGATC (SEQ ID NO: 5) to provide a canonical Shine-Dalgarno sequence. Sc-$tRNA^{Trp}_{Amb}$ was replaced by $tRNA^{SecUx}$ and $tRNA^{UTu}$ to express the $tRNA^{Sec}$ variants from the strong leuP promoter. TAG and AGC codons were introduced at position 39 by QuikChange site directed mutagenesis. pAz-C112X-AU was constructed similarly replacing the folA gene with a synthetic DNA fragment containing the azu gene from Pseudomonas aeruginosa encoding azurin codon optimized for expression in E. coli with a C-terminal His6-tag. TAG and AGC codons were introduced at position 112 by QuikChange site directed mutagenesis. pGPx-U49-AU was constructed by replacing the folA gene with a synthetic DNA fragment containing the human gpx 1 gene encoding cellular glutathione peroxidase (GPx-1) codon optimized for expression in E. coli with an N-terminal His6-tag.

Library Construction and Selection

A 1518 bp fragment encompassing the MB1 origin of replication and rop gene was amplified from pETDuet-1 (Novagen). This was assembled with a synthetic DNA fragment containing a codon optimized ble gene from *Streptoalloteichus hindustans* conferring Zeocin resistance flanked by the EM7 promoter and the endogenous terminator sequence and a MCS including NotI and NcoI sites to generate plasmid pMB1-Z. A 410 bp fragment including the selC gene and its promoter was amplified from *E. coli* DH10B genomic DNA with flanking NotI and NcoI sites and ligated into pMB1-Z to construct pMB1-ZU. Functionality of the selC gene was confirmed by complementing *E. coli* DH10B deleted for selC (DHΔc) as measured by benzyl viologen assay.

The tRNA$^{Sec}$ antideterminant library was generated by enzymatic inverse PCR using oligonucleotide primers (Table 2) to randomize the six positions identified as the main antideterminant for EF-Tu binding. Following self ligation for 16 hours, DNA was ethanol precipitated with GlycoBlue (Ambion) and transformed by electroporation into *E. coli* DHΔabc containing the plasmids pNMC-A C69X and pRSF-eSelA. Transformants were incubated in 200 ml LB medium containing 12.5 µg·mL$^{-1}$ Zeocin, 6.25 µg·mL$^{-1}$ tetracycline and 25 µg·mL$^{-1}$ kanamycin and incubated overnight. Following overnight growth, cells were diluted 1/50 in LB medium containing 6.25 µg·mL$^{-1}$ Zeocin, 3.75 µg·mL$^{-1}$ tetracycline, 12.5 µg·mL$^{-1}$ kanamycin, 1 µM Na$_2$SeO$_3$ and 20 µg·mL$^{-1}$ L-cysteine and incubated for one hour. A series of 250 µl aliquots of cells were plated on LB agar containing 6.25 µg·mL$^{-1}$ Zeocin, 3.75 µg·mL$^{-1}$ tetracycline, 12.5 µg·mL$^{-1}$ kanamycin, 1 µM Na$_2$SeO$_3$ and 20 µg·mL$^{-1}$ L-cysteine and 50-300 µg·mL$^{-1}$ ampicillin in 50 µg·mL$^{-1}$ increments. After 20 hours at 37° C. individual colonies were observed on plates containing 50-200 µg·mL$^{-1}$ ampicillin. Plasmid DNA was isolated from a selection of colonies from all plates and tRNA$^{Sec}$ mutations determined by Sanger sequencing.

three hours. Cultures were normalized to OD$_{600}$=0.1 and 5 µl aliquots plated in triplicate on LB agar containing 3.75 µg·mL$^{-1}$ tetracycline, 12.5 µg·mL$^{-1}$ kanamycin, 1 µM Na$_2$SeO$_3$, 20 µg·mL$^{-1}$ L-cysteine and a gradient of ampicillin spanning 0, 10, 25, 50, 75, 100, 150, 200, 250, 300, 350, 400, 450 and 500 µg·mL$^{-1}$. Plates were incubated at 37° C. overnight. Identical assay conditions were used to repeat this experiment with *E. coli* RTΔA.

Benzyl Viologen Assay

*E. coli* DH10B cells containing pRSFDuet-1 and pcat-pheS were used as a positive control. DHΔabcF cells harboring p15A-fdhF U140S and pRSF-UX-eSelA, and p15A-fdhF U140X and pRSF-UX-ΔSelA were used as controls for selenocysteine dependent formate dehydrogenase activity. Transformants were grown overnight at 37° C. in LB medium supplemented with 12.5 µg·mL$^{-1}$ tetracycline and 50 µg·mL$^{-1}$ kanamycin. Overnight cultures were diluted 1/20 in a final volume of 2 ml and incubated for three hours. Cultures were normalized to OD$_{600}$=0.5 and 5 µl aliquots were dotted on LB agar plates containing 3.75 µg·mL$^{-1}$ tetracycline, 12.5 µg·mL$^{-1}$ kanamycin, 5 mM sodium formate, 10 µM Na$_2$MoO$_4$, 1 µM Na$_2$SeO$_3$ and 20 µg·mL$^{-1}$ L-cysteine. Plates were incubated at 37° C. for 3 h under aerobic conditions and then transferred to anaerobic conditions at 37° C. for 60 h. Upon removal from the anaerobic chamber, plates were immediately overlaid with agar containing 1 mg·mL$^{-1}$ benzyl viologen, 250 mM sodium formate and 25 mM KH$_2$PO$_4$ at pH 7.0. Plates were photographed within 1 h of overlaying.

Optimization and Protein Purification

Initial attempts to produce selenoproteins in *E. coli* strain RTΔA.2 used an accessory plasmid derived from pRSF-UX-eSelA in which the endogenous selC promoter was replaced with the highly active *E. coli* leuP promoter in combination with an expression plasmid containing the azu gene downstream of the strong tacI promoter. Mass spectrometry of the initial selenoprotein samples revealed almost exclusive incorporation of serine at the amber codon and a number of

TABLE 2

Oligonucleotide primers for library construction. Shading represents the bases randomized to generate the antideterminant library.

| Primer | Sequence |
| --- | --- |
| selClibfwd (SEQ ID NO: 6) | TGGACTGGTCTCCCAGTTGGGGCCGCCAGCGGTCCCGGNNAGGTTC GACTCCTNNNNATCTTCCGCCAAAATGC |
| selClibrev (SEQ ID NO: 7) | GCTGGAGGTCTCaACTGGATTTAGAGTCCAGCCGCCTCACCGGAGA CGACNATCTTCCGCGCCTCG |

Rephenotyping

NotI/NcoI fragments containing tRNA$^{SecUx}$ were subcloned into pRSF-eSelA to generate pRSF-UX-eSelA. pRSF-U-eSelA variants described in Table 1 were transformed into *E. coli* DHΔabc containing the reporter plasmid pNMC-A C69TAG. DHΔabc cells containing pNMC-A and pRSFDuet-1 were used as a positive control. DHΔabc cells harboring pNMC-A C69S and pRSF-UX-eSelA, and pNMC-A C69TAG and pRSF-UX-ΔSelA were used as controls for selenocysteine dependent β-lactamase activity. Transformants were cultured overnight in LB medium containing 6.25 µg·mL$^{-1}$ tetracycline, 25 µg·mL$^{-1}$ kanamycin, 1 µM Na$_2$SeO$_3$ and 20 µg·mL$^{-1}$ L-cysteine. Following overnight growth, cells were diluted 1/10 in LB medium containing antibiotics, selenite and L-cysteine and incubated for optimizations were made to increase the ratio of Sec-tRNA$^{Sec}$ to Ser-tRNA$^{Sec}$, thought to be the main driver of incorporation efficiency. To increase the SelA to tRNA$^{Sec}$ ratio, expression of tRNA$^{Sec}$ variants was reduced by shifting the leuP cassette to the lower copy expression plasmid containing the MB1 origin of replication and adding a second selA gene downstream of the target selenoprotein. In addition, to prevent rapid depletion of the Sec-tRNA$^{Sec}$ pool following induction, the tacI promoter driving selenoprotein expression was replaced by the constitutive EM7 promoter. These changes generated expression plasmids pDHFR-P39X-AU and pAz-C112X-AU.

To further reduce the pool of Ser-tRNA$^{Sec}$ available to participate in canonical translation, the pstK gene encoding O-phosphoseryl-tRNA$^{Sec}$ kinase was added to the accessory plasmid pRSF-eSelA to yield pRSF-eSelAK. PSTK has previously been reported (Aldag et al., 2013) to increase selenocysteine incorporation with tRNA$^{UTu}$ by generating Sep-tRNA$^{Sec}$, an efficient substrate for SelA but poorly recognised by E. coli EF-Tu (Park et al., 2011). In conjunction, the selenium concentration in the medium was increased and L-cysteine omitted for selenoprotein production.

RTΔA.2 transformants containing pDHFR-P39X-AU and pRSF-eSelAK were cultured ON in LB medium containing 100 µg·mL$_{-1}$ ampicillin, 50 µg·mL$_{-1}$ kanamycin and 1 µM Na$_2$SeO$_3$. Overnight cultures were diluted ⅟500 in a final volume of 2 L LB medium containing 50 µg·mL$^{-1}$ ampicillin, 25 µg·mL$^{-1}$ kanamycin and 5 µM Na$_2$SeO$_3$ and incubated with agitation for 24 hours at 37° C. Cells were harvested by centrifugation at 8000×g for 10 min and resuspended in 20 mL of wash buffer (100 mM Tris, 150 mM NaCl, 1 mM EDTA at pH 8.0) with protease inhibitor cocktail (cOmplete, mini EDTA free, Roche) and lysozyme at 1 mg·mL$^{-1}$. Following a 20 min incubation at 4° C. cells were lysed by sonication (Model 500, Fisher Scientific) and clarified by three times by centrifugation at 35000×g for 30 min. Lysate was passed through a 0.2 µm filter and seleno-DHFR recovered using Strep-Tactin affinity chromatography following the manufacturer's instructions (GE Healthcare). Eluate was concentrated to 3 mL and dialyzed against 50 mM NH$_4$Ac pH 6.5 prior to the isolation of seleno-DHFR by size exclusion FPLC (ÄKTA, GE Healthcare). Seleno-DHFR was produced using tRNA$^{SecUx}$ with a yield of 68 µg·L$^{-1}$ and 100% incorporation efficiency. Seleno-DHFR was produced using tRNA$^{UTu}$ with a yield of 131 µg·L$^{-1}$ and 38.1% incorporation efficiency. DHFR containing serine at position 39 was produced with a yield of 225 µg·L$^{-1}$.

RTΔA.2 transformants containing pAz-C112X-AU and pRSF-eSelAK were cultured as described previously with the exception that 20 µM Na$_2$SeO$_3$ was added for the 24 hour incubation. Cells were harvested by centrifugation and the periplasmic fraction isolated. Briefly, cell pellets were resuspended in 50 mL of 100 mM Tris and 0.75 M sucrose at pH 7.5. Following addition of lysozyme to 1 mg·mL$^{-1}$ and protease inhibitor cocktail cells were gently agitated for 20 min at 4° C. 50 mL of 1 mM EDTA was added and samples incubated again for 20 minutes. EDTA was neutralized by addition of 3.5 mL 0.5M MgCl$_2$ during a further 20 min incubation. Spheroblasts were removed by centrifugation at 35000×g for 30 min, the periplasmic fraction passed through a 0.2 µm filter and mixed with imidazole stock solution to a final concentration of 20 mM. Seleno-azurin was recovered by IMAC using Ni-NTA resin and gravity flow columns. Eluate was concentrated and dialyzed against 50 mM NH$_4$Ac pH 6.5 prior to the isolation of seleno-azurin by size exclusion FPLC. Seleno-azurin was produced using tRNA$^{SecUx}$ with a yield of 50 µg·L$^{-1}$ and greater than 76% incorporation efficiency. This value likely under represents the actual level of selenocysteine incorporation as seleno-azurin was observed to form higher molecular weight complexes during and after purification, resulting in loss during size exclusion chromatography. No aggregation was observed for azurin samples containing only serine.

RTΔA.2 transformants containing pGPx-U49-AU and pRSF-eSelAK were cultured as described previously for azurin. Cells were harvested by centrifugation and resuspended in 50 mL of buffer (50 mM Potassium Phosphate, 150 mM NaCl, 10% glycerol, 1 mM DTT at pH 8.0) and lysozyme at 1 mg·mL$^{-1}$. Cells were lysed by sonication and clarified prior to GPx-1 recovery by IMAC. Eluate was concentrated and dialyzed against 100 mM phosphate buffer pH 8.0, 0.1% Tween 20 and 1 mM DTT followed by isolation of GPx-1 by anion exchange chromatography (Q HP column). GPx-1 was produced with a yield of 500 µg·L$^{-1}$ and close to 100% selenocysteine incorporation efficiency.

Mass Spectrometry

Intact protein samples were analyzed using methods described previously (Ellefson et al., 2014). Azurin, DHFR and GPx-1 samples were buffer exchanged into LC-MS grade water using 10 kDa molecular weight cutoff filters. Once the buffer exchange was complete the samples were diluted to 20 µM in a methanol/water/formic acid (50/49/1) solution. After dilution, protein solutions were infused into an Orbitrap Elite mass spectrometer (Thermo Fisher Scientific Instruments, Bremen, Germany) at a rate of 3 µL×min$^{-1}$ via electrospray ionization. In order to confirm the incorporation of selenocysteine, intact mass analysis was carried out at 240 k resolution and averaging 20 scans. Characterization of the protein sequences was undertaken by ultraviolet photodissociation (UVPD) using a 193 nm excimer laser (Coherent, Inc.) which was interfaced to the Orbitrap mass spectrometer as described previously (Shaw et al., 2013). For each UVPD spectrum, two laser pulses of 2.5 mJ were used and 250 scans were averaged. MS1 spectra were deconvoluted using the Xtract deconvolution algorithm (Thermo Fisher Scientific). UVPD mass spectra were also deconvoluted using Xtract and then analyzed using ProsightPC 3.0. Proteins containing selenocysteine were searched by adding a modification of 62.9216 Da to the serine at position 112 for azurin or 61.9146 Da for the serine at position 39 for DHFR (with subtraction of one hydrogen atom from the DHFR modification because a selenyl-sulfhydryl bond is formed when selenocysteine is present). Incorporation efficiencies were calculated by dividing the area of the modified protein peak by the summed areas of the unmodified protein peak and the modified protein peak. The peak area used for each protein was the sum of the integrated areas of the five most abundant peaks from each isotope cluster.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Aldag, et al., *Angew Chem Int Ed Engl* 2013, 52, 1441.
Armishaw, et al., *J Biol Chem* 2006, 281, 14136.
Arner, et al., *J Mol Biol* 1999, 292, 1003.
Baron and Bock, *J Biol Chem* 1991, 266, 20375.
Clark, et al., *Methods Enzymol* 2009, 462, 97.
Copeland, P. R. *Genome Biol* 2005, 6, 27.

Datsenko and Wanner, *Proc Natl Acad Sci USA* 2000, 97, 6640.
Ellefson, et al. *Nat Biotechnol* 2014, 32, 97.
Hughes and Ellington, *Nucleic Acids Res* 2010, 38, 6813.
Isaacs, et al., *Science* 2011, 333, 348.
Itoh, et al., *Science* 2013, 340, 75.
Lajoie, et al., *Science* 2013, 342, 357.
Leibundgut, et al., *Embo J* 2005, 24, 11.
Li and Yams, *J Mol Biol* 1992, 223, 9.
Majiduddin and Palzkill, *Antimicrob Agents Chemother* 2003, 47, 1062.
Mansell, et al., *Embo J* 2001, 20, 7284.
Mukai, et al., *Nucleic Acids Res* 2010, 38, 8188.
Paleskava, et al., *J Biol Chem* 2010, 285, 3014.
Park, et al. *Science* 2011, 333, 1151.
Rudinger, et al., *EMBO J.* 1996, 15, 650.
Sawers, et al., *J Bacteriol* 1991, 173, 4983.
Schlensog et al., *J Biol Chem* 1994, 269, 19590.
Schrader and Uhlenbeck, *Nucleic Acids Res* 2011, 39, 9746.
Shaw, et al. *J Am Chem Soc* 2013, 135, 12646.
Shchedrina, et al., *Proc Natl Acad Sci USA* 2007, 104, 13919.
Suppmann, et al., *Embo J* 1999, 18, 2284.
Swarén, et al., *J Biol Chem* 1998, 273, 26714.
Thyer, et al., *J Am Chem Soc* 2013, 135, 2.
Villafranca, et al., *Biochemistry* 1987, 26, 2182.
Wang and Schultz, *Chem Biol* 2001, 8, 883.
Yoshizawa, et al., *Nat Struct Mol Biol* 2005, 12, 198.
Yuan, et al., *FEBS Lett* 2010, 584, 342.
Zinoni, et al., *Proc Natl Acad Sci USA* 1987, 84, 3156.

What is claimed is:

1. A recombinant nucleic acid molecule, wherein the molecule encodes a tRNA and is at least 90% identical to SEQ ID NO: 18, and comprising one or more of the following features:
   (i) a G or C at a position corresponding to position 7;
   (ii) a T at a position corresponding to position 49;
   (iii) a A or C at a position corresponding to position 50;
   (iv) a T at a position corresponding to position 64;
   (v) a G or A at a position corresponding to position 65; and/or
   (vi) a G, T or C at a position corresponding to position 66.

2. The recombinant nucleic acid molecule of claim 1, wherein the molecule encodes a tRNA and is at least 90% identical to SEQ ID NO: 18; and comprises one or more of the following features:
   (i) a G at a position corresponding to position 7;
   (ii) a T at a position corresponding to position 49;
   (iii) a C at a position corresponding to position 50;
   (iv) a T at a position corresponding to position 64;
   (v) a G at a position corresponding to position 65; and/or
   (vi) a C at a position corresponding to position 66.

3. The recombinant nucleic acid molecule of claim 2, wherein the molecule comprises 2, 3, 4, 5 or 6 of the following features:
   (i) a G at a position corresponding to position 7;
   (ii) a T at a position corresponding to position 49;
   (iii) a C at a position corresponding to position 50;
   (iv) a T at a position corresponding to position 64;
   (v) a G at a position corresponding to position 65; and/or
   (vi) a C at a position corresponding to position 66.

4. The recombinant nucleic acid molecule of claim 2, wherein the molecule encodes a tRNA and is at least 95% identical to SEQ ID NO: 18.

5. The recombinant nucleic acid molecule of claim 4, wherein the molecule encodes a tRNA and comprises the sequence of SEQ ID NO: 18.

6. A transgenic bacterial cell, said cell comprising the recombinant nucleic acid molecule in accordance with claim 1.

7. A method of producing a commercial polypeptide comprising at least a first selenocysteine position comprising:
   (i) obtaining a bacterial cell according to claim 6 and an expression cassette encoding the commercial polypeptide; and
   (ii) incubating the bacterial cell in conditions that allow expression of the recombinant nucleic acid molecule and the commercial polypeptide.

* * * * *